US011337795B2

United States Patent
Ellis

(10) Patent No.: US 11,337,795 B2
(45) Date of Patent: *May 24, 2022

(54) INTRAOCULAR LENS INCLUDING SILICONE OIL

(71) Applicant: JelliSee Ophthalmics Inc., McLean, VA (US)

(72) Inventor: Forrest J. Ellis, McLean, VA (US)

(73) Assignee: JelliSee Ophthalmics Inc., McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/378,673

(22) Filed: Jul. 17, 2021

(65) Prior Publication Data

US 2022/0015892 A1 Jan. 20, 2022

Related U.S. Application Data

(60) Provisional application No. 63/053,134, filed on Jul. 17, 2020.

(51) Int. Cl.
| | |
|---|---|
| *A61F 2/16* | (2006.01) |
| *C08L 83/04* | (2006.01) |
| *C08L 25/16* | (2006.01) |
| *C08K 5/549* | (2006.01) |

(52) U.S. Cl.
CPC ............ *A61F 2/1618* (2013.01); *C08K 5/549* (2013.01); *C08L 25/16* (2013.01); *C08L 83/04* (2013.01); *A61F 2002/169* (2015.04); *A61F 2210/0071* (2013.01); *A61F 2210/0076* (2013.01)

(58) Field of Classification Search
CPC .............................. A61F 2/1635; C08L 83/04
See application file for complete search history.

(56) References Cited

U.S. PATENT DOCUMENTS

| 7,857,848 B2 | 12/2010 | Mentak |
| 7,985,253 B2 | 7/2011 | Cumming |
| 8,216,310 B2 | 7/2012 | Hu et al. |
| 8,232,363 B2 | 7/2012 | Hu et al. |

(Continued)

FOREIGN PATENT DOCUMENTS

WO WO-2018081595 A1 * 5/2018 ........... A61F 2/1648

OTHER PUBLICATIONS

PCT International Search Report and Written Opinion for corresponding International Application Serial No. PCT/US2021/042112, dated Nov. 9, 2021, pp. 1-13.

*Primary Examiner* — Javier G Blanco
(74) *Attorney, Agent, or Firm* — Tarolli, Sundheim, Covell & Tummino LLP

(57) ABSTRACT

An intraocular lens (IOL) having an optical axis extending in an anterior-posterior direction and an equator extending in a plane substantially perpendicular to the optical axis is described. The IOL includes: an elastic anterior face located anterior to the equator; a posterior face located posterior to the equator, wherein the anterior face, the posterior face, or both comprises a poly(dimethylsiloxane) elastomer having a durometer between about 20 Shore A to about 50 Shore A; and a chamber located between the anterior face and the posterior face comprising a silicone oil comprising polysiloxanes comprising diphenyl siloxane and dimethyl siloxane units, the silicone oil having a maximum viscosity of about 800 cSt at 25° C.

12 Claims, 7 Drawing Sheets

(56) References Cited

U.S. PATENT DOCUMENTS

| | | | |
|---|---|---|---|
| 8,481,667 B2 | 7/2013 | Hu et al. | |
| 8,530,590 B2 | 9/2013 | Hu et al. | |
| 8,900,298 B2 | 12/2014 | Anvar et al. | |
| 9,156,949 B2 | 10/2015 | Hu et al. | |
| 9,339,373 B2 | 5/2016 | Hu et al. | |
| 9,534,088 B2 | 1/2017 | Hu et al. | |
| 10,526,353 B2 | 1/2020 | Silvestrini | |
| 10,709,549 B2 | 7/2020 | Argento et al. | |
| 10,835,383 B2 | 11/2020 | Frankle et al. | |
| 10,898,316 B2 | 1/2021 | Ellis | |
| 10,980,629 B2 | 4/2021 | Anvar et al. | |
| 2011/0118834 A1* | 5/2011 | Lo | G02C 7/08 351/159.68 |
| 2011/0208301 A1* | 8/2011 | Anvar | C08G 77/34 623/6.13 |
| 2016/0157996 A1* | 6/2016 | Dolla | A61F 2/1635 623/6.13 |
| 2017/0342096 A1* | 11/2017 | Silvestrini | C08G 77/24 |
| 2018/0153682 A1 | 6/2018 | Hajela et al. | |
| 2019/0125523 A1 | 5/2019 | Barzilay | |
| 2020/0157124 A1 | 5/2020 | Silvestrini | |
| 2020/0345481 A1 | 11/2020 | Ellis | |
| 2021/0100652 A1 | 4/2021 | Walz et al. | |

\* cited by examiner

INTRAOCULAR LENS INCLUDING SILICONE OIL

CROSS-REFERENCE TO RELATED APPLICATIONS

The present application claims priority to U.S. Provisional Application No. 63/053,134, filed on Jul. 17, 2020, which is incorporated herein in its entirety.

TECHNICAL FIELD

The present disclosure relates to an accommodative intraocular lens that includes a chamber comprising a silicone oil comprising polysiloxanes comprising diphenyl siloxane and dimethyl siloxane units that improve the response time of the intraocular lens.

BACKGROUND

The human crystalline lens can be affected by one or more disorders or conditions that reduces its function and/or reduces the clarity of the lens. A common condition that occurs with aging is the gradual opacification and reduced transparency of the lens of the eye. This condition is termed a cataract. Surgical removal of a cataractous lens and placement of an artificial replacement lens (such as an intraocular lens ("IOL")) within the eye is a common surgical procedure. The development of a suitable IOL that can provide the optical quality and accommodation provided by the youthful biological lens has not been developed.

There are generally two classes of IOLs that have been developed that attempt to overcome the lack of accommodation of an IOL used to replace the natural lens when cataract surgery is performed: pseudo-accommodating lenses and accommodating lenses. A pseudoaccommodating lens can be a multiple focal point lens that uses a ring for distance focus and one or more center optics for intermediate and near focus. Other designs use diffraction optics to obtain a range of focus or use optics to achieve an extended depth of focus (EDOF). Multi-focus optics, diffraction optics, and EDOF optic IOLs can result in disruptive optical aberrations such as glare, halos, reduced contrast sensitivity, etc. Centration of these lenses within the capsular bag is important to their best visual function. These lenses use non-deforming optical elements and do not achieve the visual quality of a natural, youthful lens of the human eye. The accommodating class of IOLs includes a silicone elastomeric hinged lens that allows forward movement of the optic when the eye focuses at near. These lenses are typically placed in the lens capsular bag (the remaining thin layer of basement membrane that is the outermost layer of the natural lens and is typically left in place when the contents of the lens are removed during cataract surgery). Due to progressive fibrosis and stiffening of the lens capsule following cataract removal, the effective accommodation with these lenses is known to diminish over time. Overall, these lenses may be adequate for distance and intermediate vision, but only provide accommodation of about two diopters at most and this value has been shown to diminish over time.

Shaped haptics, levers, or other mechanical elements have been described to translate the axial compressive force along the optical axis exerted by the elasticity of the lens capsule and/or the radial compressive force exerted by the ciliary muscles to affect a desired axial displacement of the IOL optic. Additional examples may also provide flexible hinge regions of the haptic to facilitate axial displacement of an IOL. Several examples include annular ring elements in contact with the lens capsule and that use the axial compression of applied force by the capsule along the optical axis to affect axial displacement of the IOL optic. However, these IOLs are configured to be generally of fixed optical power and in line with the optical axis of the eye. As such, the axial displacement of the optical elements of these IOLs that is possible limits the dioptric power change attained. Some single or multiple optic lenses have incorporated a shape changing and axial displacement changing combination of lenses, such as a shape changing optic coupled to zonular contact haptics whereby axial compression of the lens capsule along the optical axis during accommodation results in both anterior displacement of the flexible optic, as well as compression of the sides of the optic. Other described IOLs rely on a posterior flexible region separated from a flexible anterior lens by an articulating member about the circumference.

Surface shape changing lenses are more likely to result in greater degrees of dioptric power change. These lenses include lenses with fluid filled chambers that rely on axial compression along the optical axis by the lens capsule to force fluid from one chamber into a central lens and thereby change the shape and therefore the optical surface power of the lens. Other lenses use the compressive force by the lens capsule to provide a radial compressive force about the equatorial periphery of a flexible lens to shape change the lens. These are generally two-part systems with a circumferential haptic design with a central fixed posterior lens that fits within the capsule and then a separately placed pliable optic secured within the outer haptic ring. Compression by the "elastic" lens capsule is meant to provide an axial compressive force along the optical axis to the central lens flexible optic. Other IOLs use a compressive force exerted on rigid haptics to compress a pliable optic against a separate fixed power posterior lens. These IOLs rely on the shape change of the posterior surface of the pliable optical element pressed against a fixed optical element or pressed against a relatively rigid posterior lens capsule to alter the dioptric power of the lens system. Other IOLs incorporate a skirt with a capsular contact ring. Such IOLs rely on compression exerted by the "elastic" lens capsule to impart a compressive force on a capsular contact ring and the mechanical design of this ring pulls radially about the equator of the IOL's flexible optic. Again, because these IOLs rely on retained capsular elasticity/pliability and because it is generally known that the lens capsule following cataract surgery becomes less pliable and more fibrotic, it is unlikely these lenses will retain accommodating/dis-accommodating ability. None of the shape changing accommodating IOLs described above mimic the natural human lens during accommodation or effectively account for the inevitable loss of capsular elasticity/pliability and progressive fibrosis and stiffening of the lens capsule.

Intraocular lenses ("IOL") may comprise a bulk polymeric material with one or more fluids disposed therein. For example, some accommodating IOLs use fluid movement within the IOL, or a change in fluid pressure within the IOL, to effect optical power change in the IOL. Silicone oil is an example of a fluid that can be used in an IOL. When fluids, such as silicone oil are used in an accommodating intraocular lens, the fluid, over time, may tend to swell into the bulk material. This can alter the physical properties of the bulk material. It is therefore desirable to minimize the amount of swelling into the bulk material. It may also be important to provide silicone oil that does not reduce the response time of the accommodating IOL.

Accommodating IOLs can utilize the eye's natural ciliary muscle movements to provide accommodation in the IOL. For example, some accommodating IOLs are implanted within a patient's capsular bag (after the native lens contents have been removed) and respond radial forces applied to the lens capsule by the ciliary muscle via the zonules to change the power of the IOL. Some IOLs are designed to be implanted outside of the lens capsule and accommodate in other ways. Whatever the method of accommodation, silicone oil disposed within an accommodating IOL can be adapted to be moved within the IOL when the bulk polymeric material changes shape. Properties of the silicone oil can therefore affect the accommodative response time of the IOL. Improved fluids (e.g., silicone oils) and their methods of use in accommodating intraocular lenses are therefore needed.

SUMMARY OF THE INVENTION

The present disclosure relates to ophthalmic devices including IOLs and more particularly to accommodating intraocular lenses (accommodating IOLs) including a silicone oil disposed within the chamber of the lens. In one aspect, an intraocular lens (IOL) having an optical axis extending in an anterior-posterior direction and an equator extending in a plane substantially perpendicular to the optical axis is provided. The IOL includes: an elastic anterior face located anterior to the equator; a posterior face located posterior to the equator, wherein the anterior face, the posterior face, or both comprises a poly(dimethylsiloxane) elastomer having a durometer between about 20 Shore A to about 50 Shore A; and a chamber located between the anterior face and the posterior face comprising a silicone oil comprising polysiloxanes comprising diphenyl siloxane and dimethyl siloxane units, the silicone oil having a maximum viscosity of about 800 cSt (i.e., mm²/s) at 25° C. In some embodiments, the IOL further comprises an elastic side wall extending across the equator and extending from the anterior face to the posterior face.

In some embodiments, the poly(dimethylsiloxane) elastomer has a durometer of about 50 Shore A. In additional embodiments, the anterior and posterior face of the IOL comprise polysiloxane that is at least 99% poly(dimethylsiloxane) elastomer. In further embodiments, the anterior face and the posterior face have one or more surfaces that are highly smooth. In yet further embodiments, at least a portion of the anterior face and the posterior face are coated with a layer of parylene.

The silicone oil disposed within the chamber of the lens can have a variety of different characteristics. In one embodiment, the silicone oil has a viscosity between about 400 cSt at 25° C. to about 800 cSt at 25° C. In another embodiment, the silicone oil has a refractive index between 1.49-1.53. In some embodiments, the silicone oil comprises less than 0.1% octamethylcyclotetrasiloxane, decamethylcyclopentasiloxane, and dodecamethylcyclohexasiloxone. In further embodiment, the silicone oil comprises long chain polysiloxane molecules. In yet further embodiments, the polysiloxane comprises at least 10 mol % diphenyl siloxane. In additional embodiments, the silicone oil comprises about 30 mol % diphenyl siloxane and about 70 mol % dimethyl siloxane. In yet further embodiments, the silicone oil has a mean molecular weight from 1,000 to about 3,000 Daltons.

DETAILED DESCRIPTION OF THE INVENTION

Figure 1:
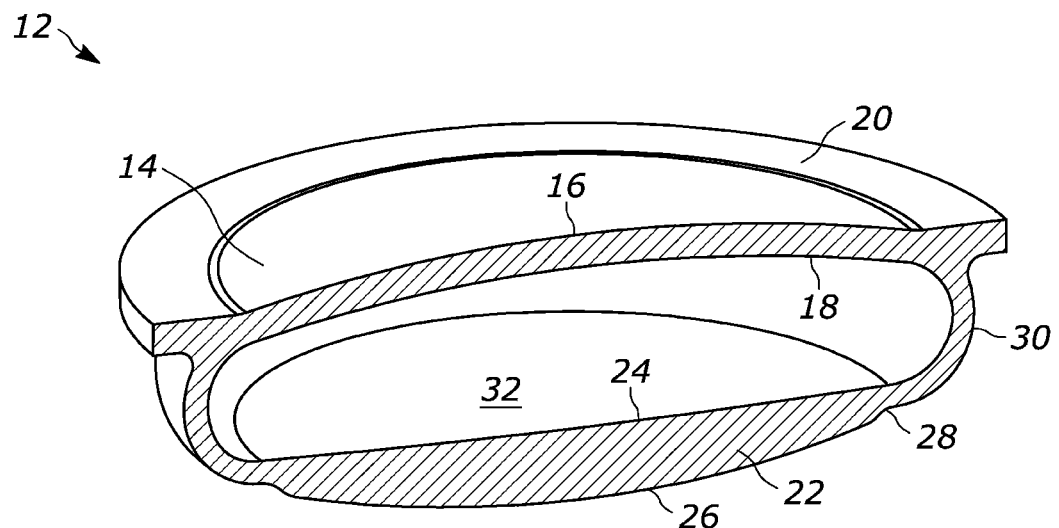
FIG. 1 is a perspective cross-sectional view of a shape-changing optic of an IOL according to an aspect of the present disclosure.

The present invention provides an intraocular lens (IOL) having an optical axis extending in an anterior-posterior direction and an equator extending in a plane substantially perpendicular to the optical axis. The IOL includes: an elastic anterior face located anterior to the equator; a posterior face located posterior to the equator, wherein the anterior face, the posterior face, or both comprises a poly (dimethylsiloxane) elastomer having a durometer between about 20 Shore A to about 50 Shore A; and a chamber located between the anterior face and the posterior face comprising a silicone oil comprising polysiloxanes comprising diphenyl siloxane and dimethyl siloxane units, the silicone oil having a maximum viscosity of about 800 mm²/s at 25° C.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such. The conjunctive phrase "and/or" indicates that either or both of the items referred to can be present.

By "substantially" is meant that the shape or configuration of the described element need not have the mathematically exact described shape or configuration of the described element but can have a shape or configuration that is recognizable by one skilled in the art as generally or approximately having the described shape or configuration of the described element.

As used herein, the terms "anterior," "posterior," "superior," "inferior," "lateral," and "medial" refer to the position of elements when a patient is in a standard anatomical position unless otherwise indicated. The terms "left," "right," "top" and "bottom" refer to the position of elements as they are depicted in the drawings and the terms "left" and "right" can be interchanged unless indicated otherwise.

The terms "first," "second," etc. are used to distinguish one element from another and not used in a quantitative sense unless indicated otherwise. Thus, a "first" element described below could also be termed a "second" element. A component operably coupled to another component can have intervening components between the components so long as the IOL can perform the stated purpose.

By "integral" or "integrated" is meant that the described components are fabricated as one piece or multiple pieces affixed during manufacturing or the described components are otherwise not separable using a normal amount of force without damaging the integrity (i.e., tearing) of either of the components. A normal amount of force is the amount of force a user would use to remove a component meant to be separated from another component without damaging either component.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "about," when referring to a value or range is meant to encompass variations of in some embodiments ±10%, in some embodiments ±5%, in some embodiments ±1%, in some embodiments ±0.5%, and in some embodiments ±0.1% from the specified amount (and all percent values therebetween), as such variations are appropriate for the IOL to perform its desired functionality.

A "subject," as used herein, can be any animal, and may also be referred to as the patient. Preferably the subject is a vertebrate animal, and more preferably the subject is a mammal, such as a research animal (e.g., a mouse or rat) or a domesticated farm animal (e.g., cow, horse, pig) or pet (e.g., dog, cat). In some embodiments, the subject is a human.

"Biocompatible" as used herein, refers to any material that does not cause injury or death to a subject or induce an adverse reaction in a subject when placed in contact with the subject's tissues. Adverse reactions include for example inflammation, infection, fibrotic tissue formation, cell death, or thrombosis. The terms "biocompatible" and "biocompatibility" when used herein are art-recognized and mean that the material is neither itself toxic to a subject, nor degrades (if it degrades) at a rate that produces byproducts at toxic concentrations, does not cause prolonged inflammation or irritation, or does not induce more than a basal immune reaction in the host.

Any estimated molecular weights described herein are obtained relative to polystyrene molecular weights standards.

Intraocular Lens

In one aspect, the present invention provides an intraocular lens (IOL) having an optical axis extending in an anterior-posterior direction and an equator extending in a plane substantially perpendicular to the optical axis. The IOL comprises: an elastic anterior face located anterior to the equator; a posterior face located posterior to the equator, wherein the anterior face, the posterior face, or both comprises a poly(dimethylsiloxane) elastomer having a durometer between about 20 Shore A to about 50 Shore A; and a chamber located between the anterior face and the posterior face comprising a silicone oil comprising polysiloxanes comprising diphenyl siloxane and dimethyl siloxane units, the silicone oil having a maximum viscosity of about 800 $mm^2/s$ at 25° C.

All IOLs as described herein are used for medical purposes and are therefore sterile. Components of IOLs as described herein can be used with IOLs described herein as well as other IOLs. For example, an IOL as described herein can be placed anterior to an existing, previously placed IOL. IOLs include fixed power, multifocal, EDOF, diffractive and other variable focus lenses. Although the drawings show certain elements of an IOL in combination, it should be noted that such elements can be included in other embodiments or aspects illustrated in other drawings or otherwise described in the specification. In other words, each of the disclosed aspects and embodiments of the present disclosure may be considered individually or in combination with other aspects and embodiments of the disclosure including patent applications incorporated by reference herein.

Unlike shape changing accommodating IOLs described by way of background, IOLs are provided herein that can mimic the gradient elastic properties of a natural youthful human lens during accommodation and include a shape-changing optic where components of the optic change shape as the IOL transitions from an accommodated state to a dis-accommodated state and vice versa. Without wishing to be bound by a specific mechanism of action, it is considered by some that the lens capsules' "elasticity" controls and shapes the lens as a whole (the lens nucleus and cortex). On this basis, the lens contents are considered pliable. However, the volume of the lens contents compared to the thickness and known modulus of elasticity of the lens capsule predicts that the lens capsule cannot solely control and alter the shape of the lens nucleus and cortex. Finite element analysis (FEA) predicts that radial tension about the equatorial region of a lens capsule filled with a soft pliable solid or liquid does not result in significant shape change to either the anterior or posterior surface of the lens compared to what is known to occur with the natural youthful human lens. Providing radial tension directed specifically to at least the anterior face of an accommodating IOL; having that tension directed at points anterior to the equator of the IOL; the anterior face of the IOL being more resistant to deformational change than the content(s) of a chamber underlying the anterior face; the anterior face demonstrating elastic properties in so much as the anterior face deforms when a force is applied to the anterior face and the anterior face will return to its original shape with the removal of the force, results in a greater amount of anterior face shape change and therefore accommodating dioptric power change than can be achieved with a similar force applied at points at or more near the equator of the IOL (e.g. equatorial). In addition, a force applied to the anterior face at points anterior to the equator of the IOL requires less diameter change of the anterior face per diopter of power change of the IOL compared to a similar force applied at points at or more near the equator of the IOL thereby allowing the anterior face of the IOL to shape change even with very small amounts of anterior face diameter change when going from an accommodated state, a dis-accommodated state, and states in between.

In particular, in an aspect, an IOL comprising a shape changing optic that can assume an accommodated state, a dis-accommodated state, and states therebetween is provided. Components of the shape-changing optic can be deformable such that ocular compression force or tensile force applied to the optic caused by ciliary muscle contraction or relaxation causes one or more components of the optic to change shape and allows the optic to change dioptric power. As such, components of a shape-changing optic can deform or change shape when a force is applied. If a component is less resistant to deformational change than another component, the former component is more likely to, or to a greater degree, deform for a given amount of applied or removed force than the latter component. A component is more resistant to deformational change than another component, if the former component is less likely to, or to a lesser degree, deform for a given amount of applied or removed force than the latter component. It is understood that for any given component resistant to deformational change, the force applied/removed to such component does not exceed the force that results in breakage of the component such that it is no longer useful for its therapeutic purpose.

Figure 2:
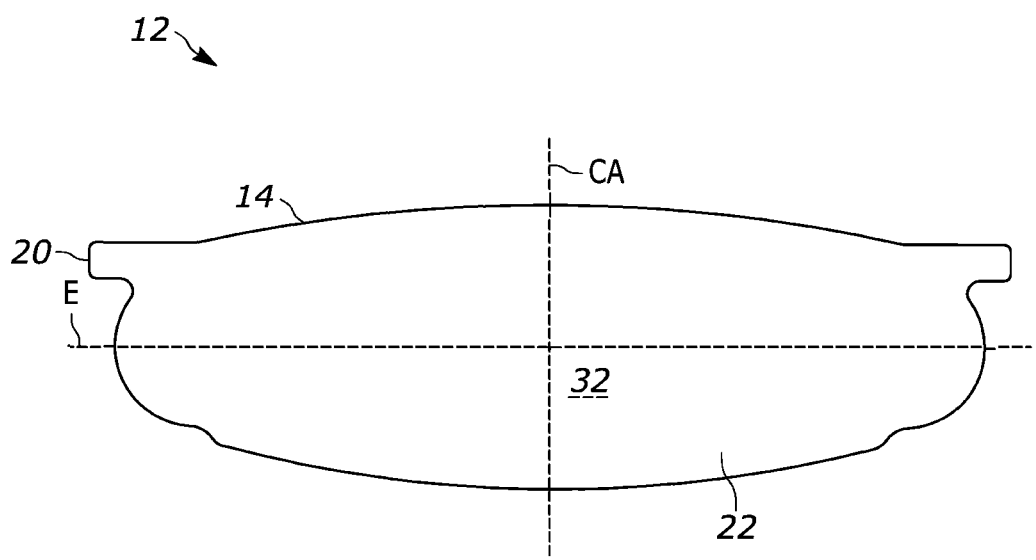
FIG. 2 is a side view of a shape-changing optic of an IOL according to an aspect of the present disclosure.
Figure 3:
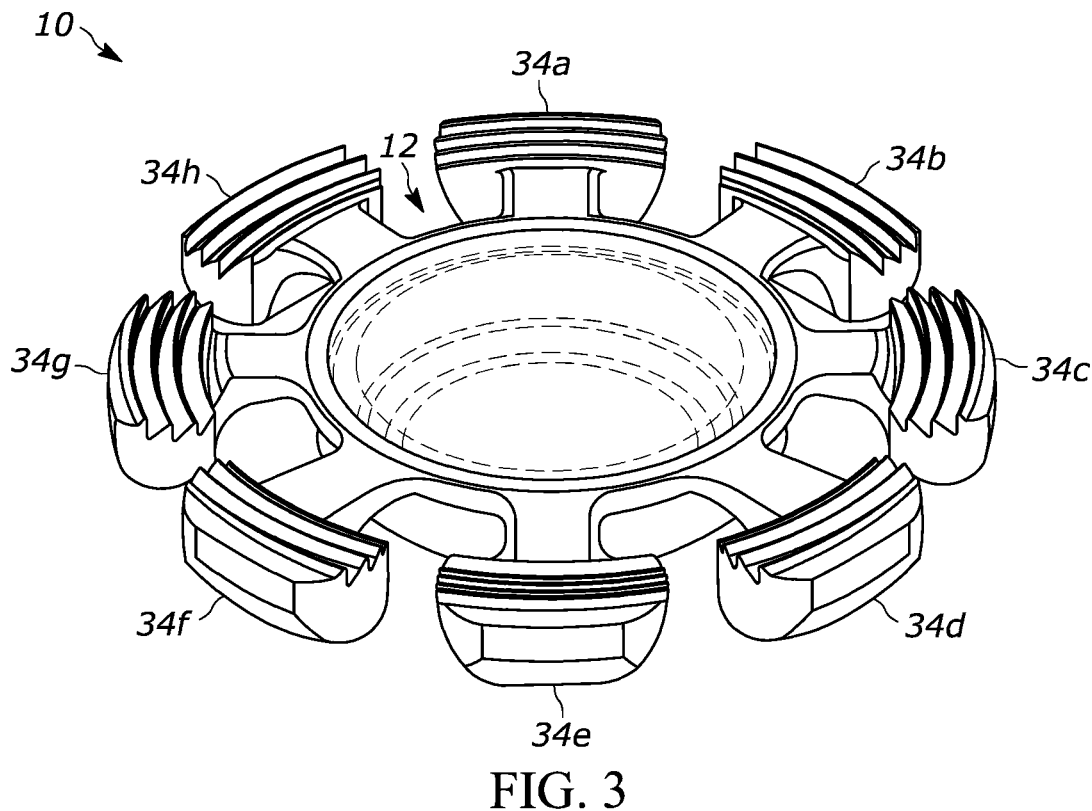
FIG. 3 is a perspective view of the IOL including the shape changing optic of FIGS. 2 and 3 including a depiction of haptics according to an aspect of the present disclosure.

FIG. 2 depicts a central or optical axis CA extending in an anterior-posterior direction and an equator E extending in a plane substantially perpendicular to the central axis. The equator is an imaginary line drawn around the circumference of a lens perpendicular to the optical axis, equally distant from the anterior face of the lens and the posterior face of the lens, dividing the lens into an anterior half and a posterior half. Referring to FIGS. 1-3, a shape-changing optic 12 of an IOL 10 can comprise an elastic anterior face 14 located anterior to equator E. Anterior face 14 can have an anterior surface 16, a posterior surface 18 and a periphery 20. Shape-changing optic 12 can also comprise a posterior face 22 having an anterior surface 24, a posterior surface 26, and a periphery 28. Shape-changing optic 12 can further include an elastic side wall 30 extending across equator E and extending from anterior face 14 to posterior face 22. A chamber 32 can be located between anterior face 14 and posterior face 22 and can house material or contents as described in more detail below. Components of the shape-changing optic can be made to be more or less resistant to deformational change by altering the thickness of the component, the type of material from which the component is fabricated, or by altering the chemical/material properties of the component material itself for example. With reference to FIG. 3, IOL 10 can further comprise at least one haptic 34 extending from the periphery of the anterior face. At least one haptic can also extend from the periphery of the posterior face, or the periphery of both the anterior face and the posterior face as described below.

Regarding specific components of an IOL, the anterior face, as stated above, can have elastic properties. Elastic properties can allow for the anterior face to change shape with an applied force, but also to return to its original configuration when the force is removed. It is beneficial that the anterior face be more resistant to deformational change (e.g. less pliable, firmer) than the contents or material contained within the chamber because when an outward radial force is applied to the anterior face, the contents of the chamber can more easily deform to allow flattening of the anterior face. Exemplary fabrication materials for the anterior face include silicone (i.e., polysiloxane), an acrylic (hydrophobic or hydrophilic) polymer, polymethylmethalcryalate (PMMA), silastic, collamer, a suitable optical thermoplastic polymer, another suitable optical material, and suitable combinations thereof.

Figure 4:
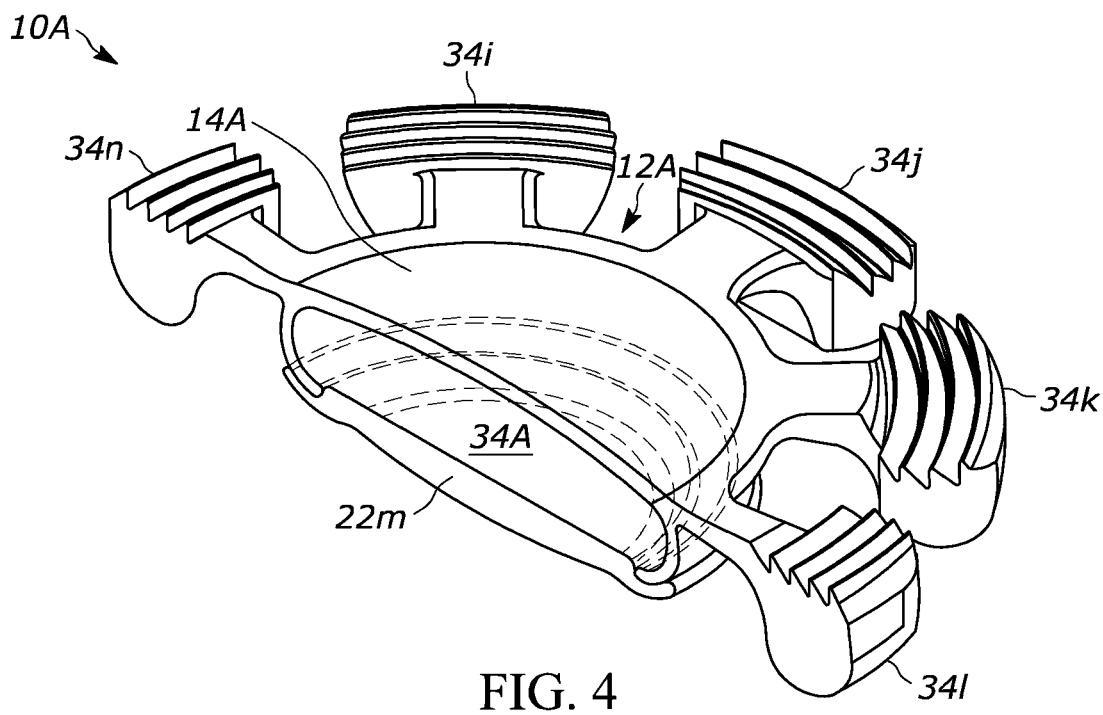
FIG. 4 is a perspective cross-sectional view of an IOL according to another aspect of the present disclosure.
Figure 5:
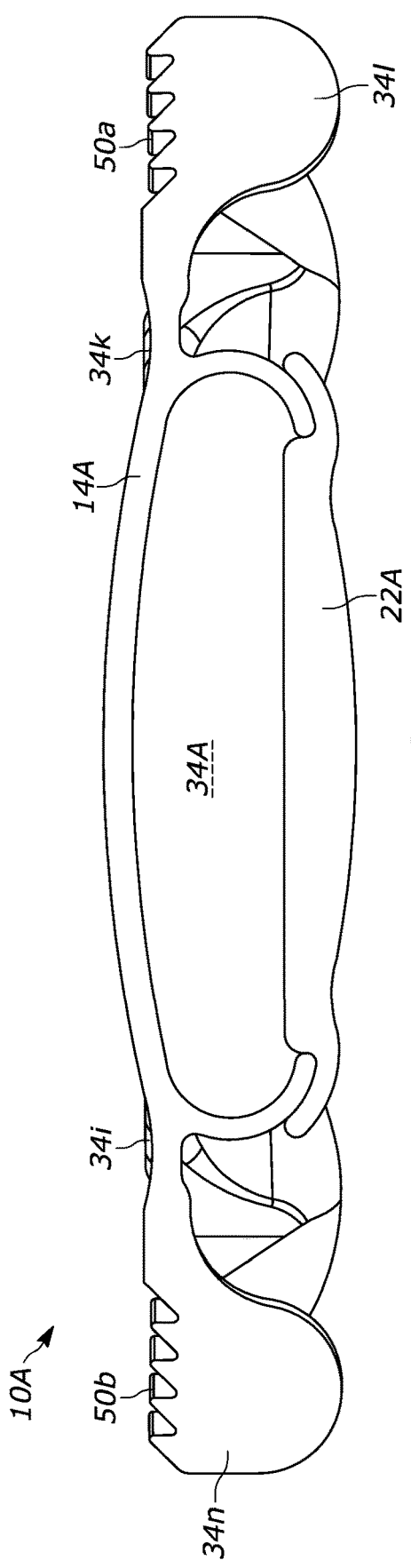
FIG. 5 is a side view of an IOL according to an aspect of the present disclosure.
Figure 6:
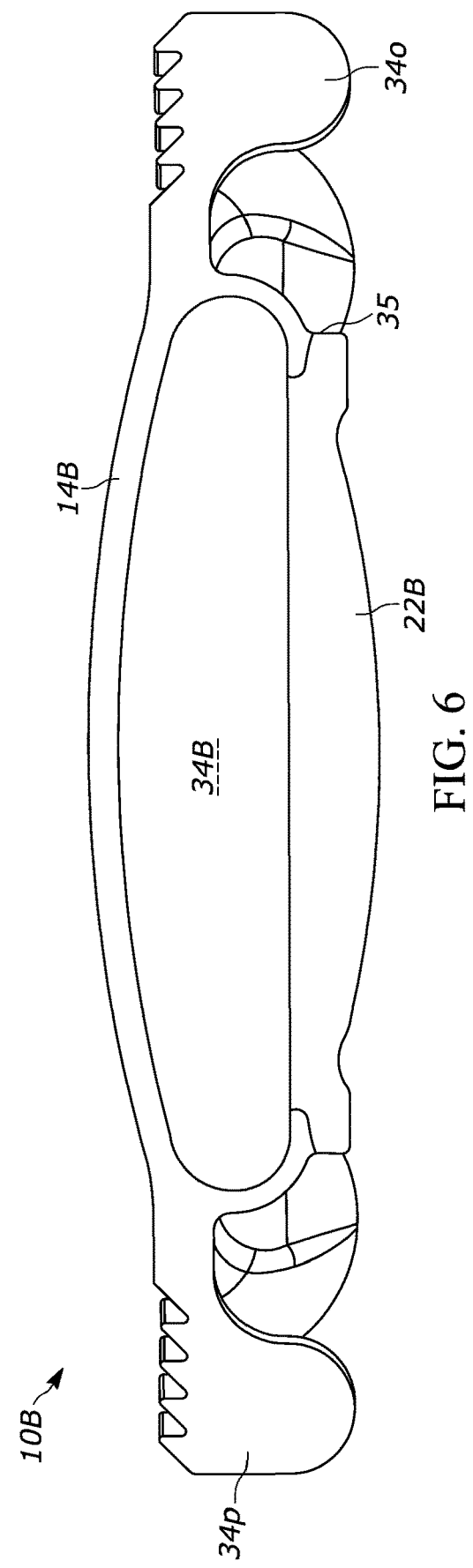
FIG. 6 is a side view of an IOL according to another aspect of the present disclosure.

Regarding the posterior face of the shape-changing optic, the posterior face can be more resistant to deformational change than the anterior face or the contents contained within the chamber of the shape-changing optic. The posterior face need not have the ability to change shape. When implanted and in certain aspects, the posterior face can rest against the posterior capsule and the vitreous substance and it may not be desirable to have those less predictable forces altering the power of the optic. Further, having a posterior face that is more resistant to deformational change than the anterior face or the contents of the chamber of the shape-changing optic can allow the posterior face optic to have a relatively more fixed power posterior lens permitting the incorporation of beneficial optical properties. In addition, a posterior face more resistant to deformational change can allow the contents of the chamber to reshape the side wall(s) when the anterior face changes shape in response to a force. The posterior face can be part of a one-piece integral IOL 10 as depicted in FIG. 1-3 or can be a two-piece integral IOL 10A as illustrated in FIG. 4-6. In certain aspects, the posterior face is elastic. Exemplary fabrication materials for the posterior face include silicone (i.e., polysiloxane), an acrylic (hydrophobic or hydrophilic) polymer, polymethylmethalcryalate (PMMA), silastic, collamer, a suitable optical thermoplastic polymer, another suitable optical material, or suitable combinations thereof. The posterior face can comprise a lens with a variety of optical properties, such as, for example, a spherical, aspheric, toric, toroidal, multifocal, diffractive, extended depth of focus, or combinations thereof. As illustrated in FIG. 6, an IOL 10B can comprise a shape-changing optic where the posterior face 22B has a squared peripheral edge 35 to reduce posterior capsular opacification, by inhibiting, for example, peripheral lens epithelial cells from migrating across the posterior face.

In some embodiments, the anterior face and/or the posterior face may have one or more surfaces that are highly smooth (i.e., has a low surface roughness). The smoothness of the surface is determined primarily by the smoothness of the mold used to prepare the anterior and/or posterior face. The finish on the molds should be of sufficient quality to produce a finish that meets the international standards of optics for intraocular lenses. As such, the finish on the molds should be at least SPI A-3, more preferably A-2, and yet more preferably A-1. SPI A-1 corresponds to 6000 grit, SPI A-2 corresponds to 3000 grit, and SPA A-3 corresponds to 1200 grit. If the surfaces are not smooth, one needs to match the refractive index of the shell polymeric material and the silicone oil to avoid optical interface aberrations. Smoothness, or surface roughness, can be measured using a contact-type roughness tester, an atomic force microscope, a while light interferometer, or a laser microscope, which provide resolutions from 1 nm to 0.1 nm.

Figure 7:
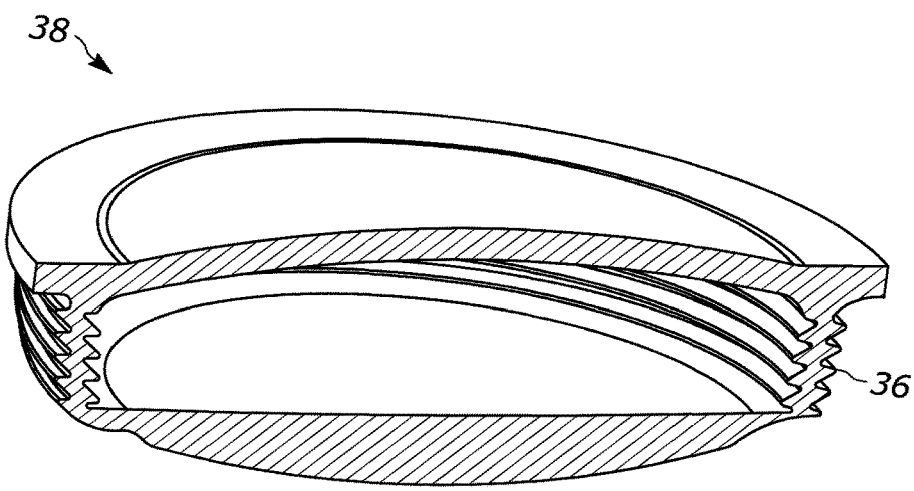
FIG. 7 is a perspective cross-sectional view of a shape-changing optic of an IOL according to an aspect of the present disclosure.
Figure 8:
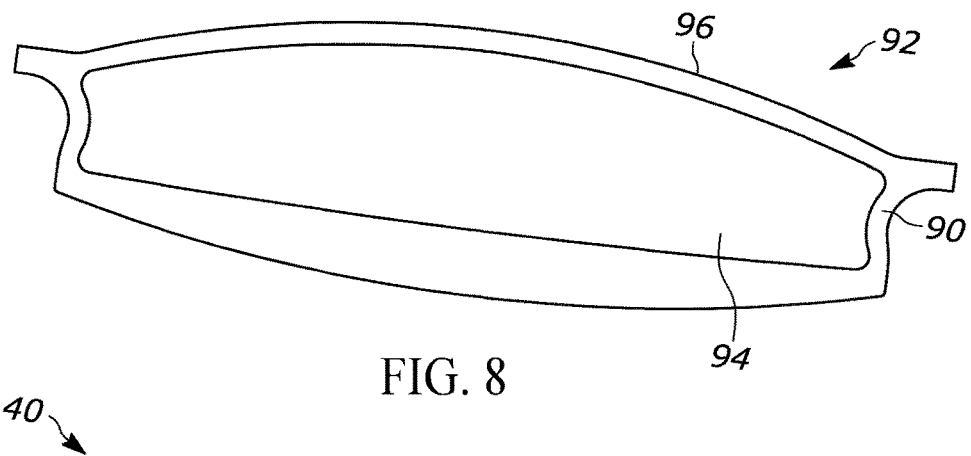
FIG. 8 is a side cross-sectional view of a shape-changing optic of an IOL according to an aspect of the present disclosure.

Regarding the side wall, as stated above, the side wall can have elastic properties. In certain aspects, the side wall can be fabricated from a material that is equal to or less resistant to deformational change than the anterior face. Such features can allow for the contents contained within the chamber to expand the area of the side wall to allow the volume of the contents of the chamber to remain the same when the anterior surface is flattened. Having the side wall deform can facilitate and allow for a greater amount of shape change to the anterior face of the shape-changing optic. Exemplary fabrication materials for the side wall include silicone, an acrylic (hydrophobic or hydrophilic) polymer, polymethylmethalcryalate (PMMA), silastic, collamer, a suitable optical thermoplastic polymer, another suitable material, or a suitable combination thereof. The side wall can also be equal to or less resistant to deformational change than the anterior face or the posterior face by being thinner than the anterior face or the posterior face. Alternatively, or in addition, the side wall 36 of a shape-changing optic 38 can be equal to or less resistant to deformational change by having a bellowed configuration as illustrated in FIG. 7. The bellows can be horizontally or vertically oriented or have other orientations to allow for peripheral side wall expansion or contraction. As illustrated in FIG. 8, the side wall 90 of a shape changing optic 92 can have a plano, concave, convex, or other configuration to facilitate displacement of the contents of chamber 94 against side wall 90 when anterior face 96 is flattened.

Figure 9:
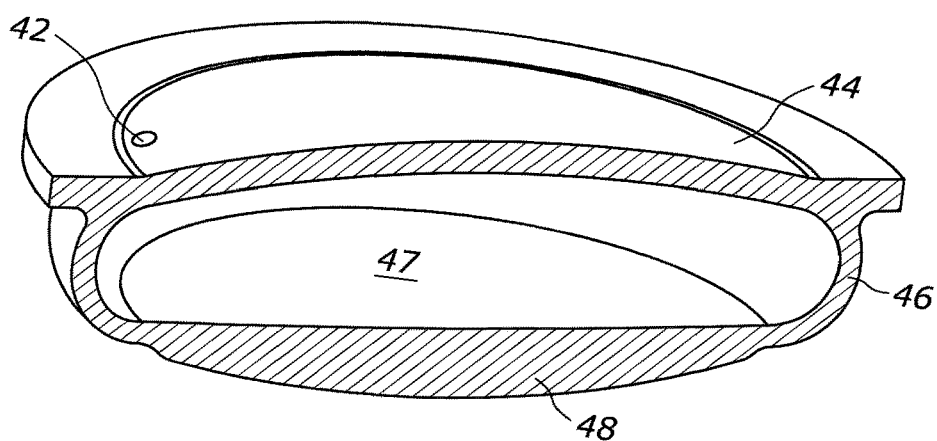
FIG. 9 is a is a side cross-sectional view of a shape-changing optic of an IOL according to an aspect of the present disclosure

Regarding the chamber, the chamber can be defined by the posterior surface of the anterior face, the anterior surface of the posterior face, and an inner surface of the side wall. The interior contents or material of the chamber can comprise a soft solid, a gel, a viscoelastic material, a flowable fluid, or a gas, or other suitable material. Exemplary materials that can be contained within the interior of the chamber include a soft silicone, or other soft material subject to deformational change, air or other gas, silicone oil (of various refractive indices), an aqueous solution of saline or hyaluronic acid, a viscoelastic polymer, polyphenyl ether, or other optical fluid, solid or gases, or suitable combinations thereof. The chamber can have an internal layer or coating to seal the contents of the chamber from the anterior face, the side wall and/or the posterior face. The chamber can be pre-loaded (e.g. by a manufacturer) with a suitable material. Alternatively, the chamber can be loaded with a suitable material by a clinician. For example, and with reference to FIG. 9, a shape-changing optic 40 of an IOL can define at least one port 42 (enlarged in FIG. 9 for purposes of clarity) sized and dimensioned to receive a needle or catheter, the needle or catheter being sized and dimensioned to deliver a fluid, gel, or gas to the chamber and/or to exchange fluid with a different material or a material having a different refractive index, for example. Although FIG. 9 illustrates the port defined by anterior face 44, the port can be defined by the side wall 46 or the posterior face 48 of the shape-changing optic. Having a port can allow a user to add or remove substance from chamber 47 to adjust the optical power of the lens. For example, by adding additional substance to the chamber, the volume of the substance can increase in the chamber resulting in an increase in the surface(s) curvature and the overall power of the lens and removing substance can decrease the volume of the substance in the chamber resulting in a decrease in the surface(s) curvature and the overall power of the lens. Also, by exchanging the substance for one with a different refractive index, the overall dioptric power and the range of accommodation of the IOL can be increased or decreased.

Regarding the at least one haptic of the IOL, such a haptic(s) is the portion of the IOL that is configured to interact with the lens capsule, the lens zonules, the ciliary muscle, or other parts of a patient's eye. The at least one haptic can be molded, shaped into, integral with, or otherwise extend from the shape-changing optic of an IOL. As illustrated in FIG. 3, the at least one haptic can comprise a plurality of haptics disposed about the circumference of the anterior face of the shape-changing optic. The at least one haptic can be elastic but can be more resistant to deformational change than the anterior face. An advantage to this is that the haptic can be firmer to provide a linear force from the haptic to the periphery of the anterior face. Without wishing to be bound by any particular mechanism of action, if the haptic were to be less resistant to deformational change than the anterior face, the radial tension could result in stretching of the haptic and less tension on the periphery of the anterior face. Thus, the anterior face may not shape change as much for a given force applied to the haptic. Exemplary fabrication materials for the at least one haptic include silicone, an acrylic (hydrophobic or hydrophilic) polymer, polymethylmethalcryalate (PMMA), silastic, collamer, a suitable optical thermoplastic polymer, another suitable material, or suitable combinations thereof.

Regarding the haptics, in certain aspects, each of the plurality of haptics is non-rotatable in response to axial compression along the optical axis on the shape-changing optic. In certain aspects, each of the haptics has a peripheral portion having a posterior face and an anterior face, with the posterior face being curved. In other aspects, the medial portion of each of the plurality of haptics medial portion extends from and is connected to the periphery of the anterior face such that the plurality of haptics changes the shape of the anterior face via application of radial force to the periphery of the anterior face in a direction perpendicular to the optical axis and not via axial compressive forces along the optical axis on the shape-changing optic or via axial compressive forces on the haptics.

FIGS. 3 to 6 illustrate an IOL where at least one haptic extends from the anterior face of a shape-changing optic. The shape-changing optic can change shape in response to an ocular force, specifically a force generated by the contraction or relaxation of the ciliary muscle of the patient's eye. The at least one haptic, interacting with the lens capsule, can apply radial outward tension to the anterior face when the ciliary muscle relaxes and radial outward tension is placed on the lens capsule via the lens zonules. The at least one haptic can be elastic but can be equal to or more resistant to deformational change than the anterior face.

Figure 10:
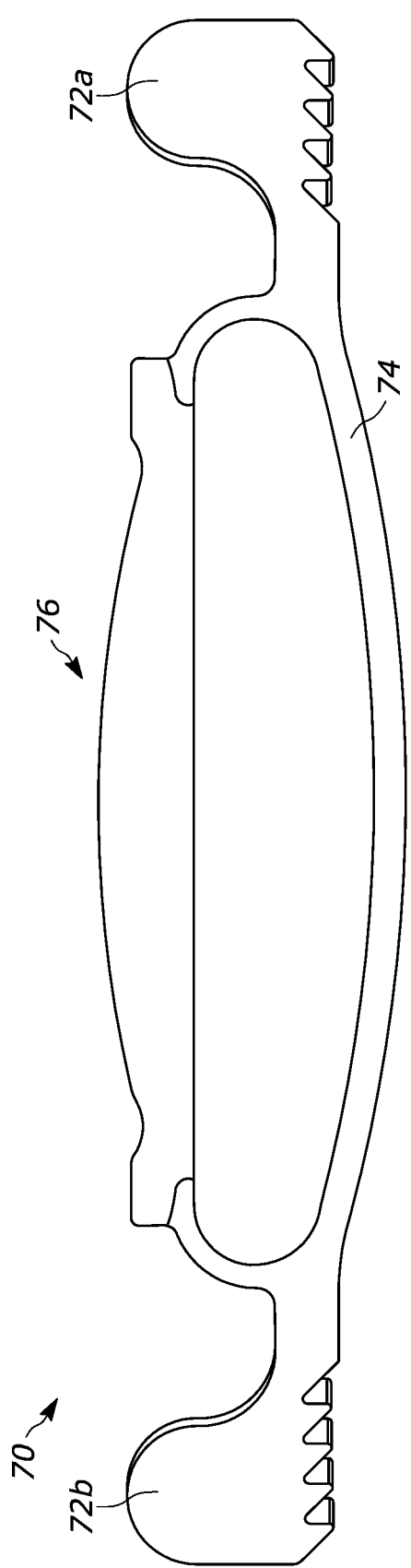
FIG. 10 is a side view of an IOL according to another aspect of the present disclosure.
Figure 11:
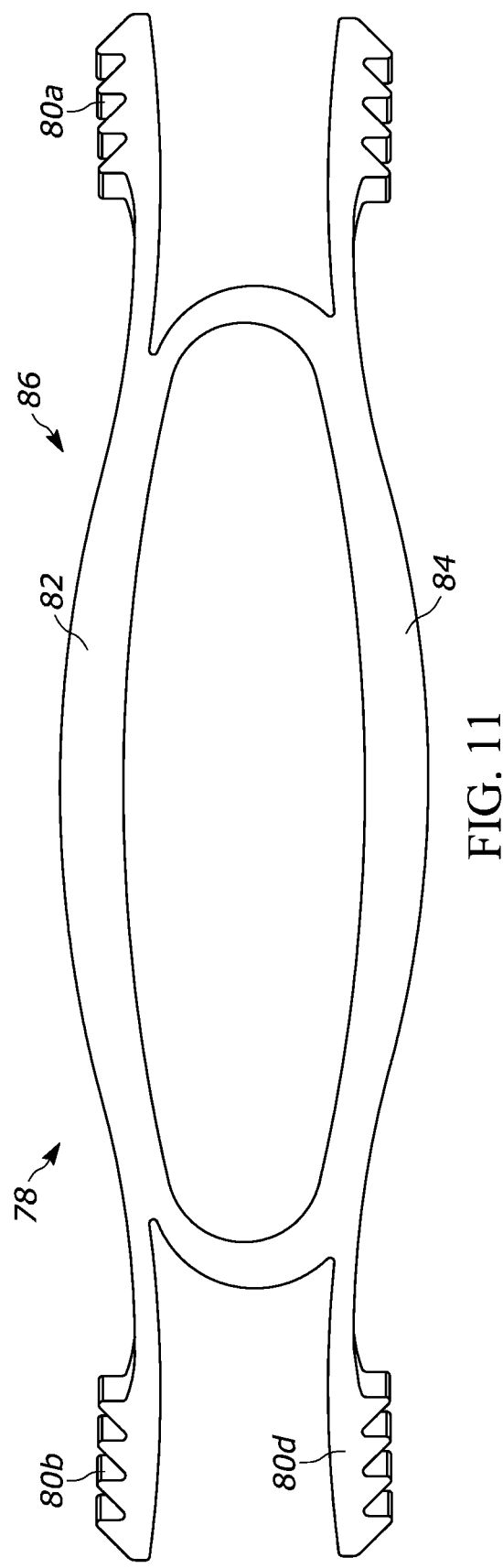
FIG. 11 is a side view of an IOL according to another aspect of the present disclosure.

FIG. 3 illustrates an aspect where a plurality of haptics extends circumferentially from the shape-changing optic. When implanted and when the ciliary muscles of a patient's eye relaxes (such as when the eye is in a dis-accommodated state), the ciliary muscles apply tensile force to the plurality of haptics (via the lens capsule with lens zonule attachments between the lens capsule and the ciliary muscles, for example). The plurality of haptics, in turn, can apply tensile force to the periphery of the anterior face at each site (referred to herein as an "extension site") where a haptic extends from the periphery of the anterior face. By having a plurality of haptics as depicted in FIGS. 3 and 4, the net result can be that the anterior face can be pulled outward from several extension sites (such as, for example, eight extension sites as illustrated in FIG. 3) and functionally result in relatively symmetric radial tension placed on the periphery of the anterior face of the shape-changing optic. Referring to FIG. 10, in certain aspects, an IOL 70 includes at least one haptic 72 extending from posterior face 74 of shape-changing optic 76. By having the force applied to the posterior face, a change in shape of the optic can be achieved independent of or in combination with a force applied to the anterior face. Referring to FIG. 11, in other aspects, an IOL 78 includes at least one haptic 80 extending from anterior face 82 and posterior face 84 of shape-changing optic 86. If a force is applied to both the posterior and the anterior faces, the total dioptric power change of the IOL for a given force can be increased. In other words, if a force is applied to both the anterior and posterior face, shape change can be obtained to both surfaces and thereby increase overall accommodation.

The at least one haptic can engage the inner surface of the lens capsule or the outer surface of the lens capsule. Referring to FIGS. 3-6, the peripheral portion of the at least one haptic 34 can comprise ridges 50 as illustrated in FIGS. 3-6 configured to engage an inner surface of a lens capsule. For example, ridges 50 can interact with the lens capsule to stabilize the haptics within the lens capsule. Ridges can also allow the haptics to interact and fixate into the lens capsule. Such an aspect can allow IOL placement within the capsular bag, while still allowing translation of tension/relaxation of the lens capsule (via the lens zonules and ciliary body) during accommodation/dis-accommodation of the lens. Current haptic designs do not allow the haptics to be positioned within the lens capsule while fixating the haptics to allow tension/relaxation on the lens capsule to translate forces into the haptics. Current haptic designs are smooth and allow the capsule and haptic to glide past each other, which does not allow the translation of forces placed on the peripheral lens capsule (via the zonules and ciliary muscle). When placing the IOL inside the capsular bag, the ridge(s) can be configured to allow the IOL to be rotated until the desired rotational position of the IOL is achieved. Once the IOL is rotated into its desired position, the forces on the haptics fixate lateral portions of the haptics to the inside peripheral edge of the lens capsule. The ridges then provide resistance to these forces and facilitate the forces from the ciliary body, zonules, and lens capsule into a force on the haptic(s).

Figure 12:
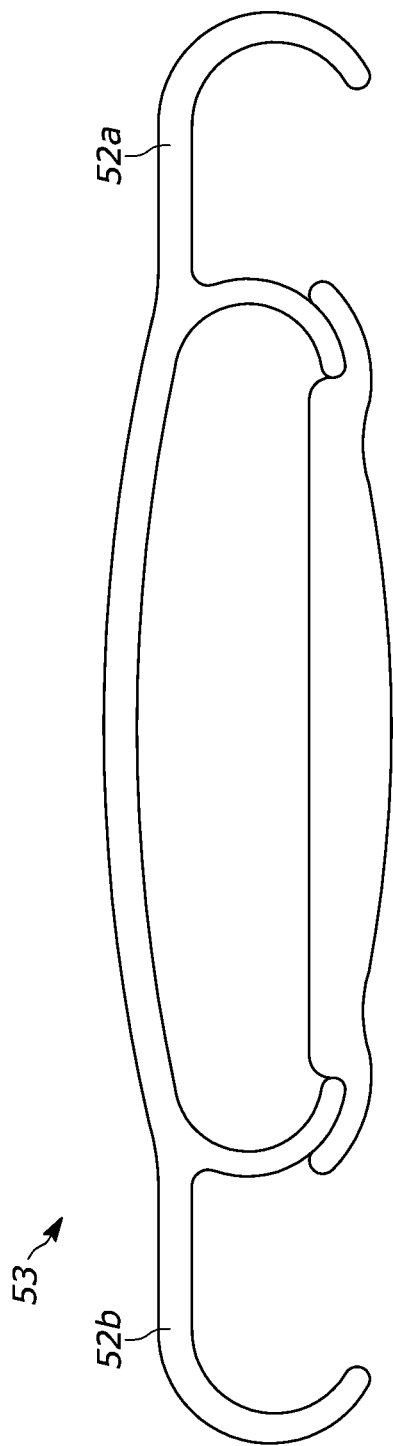
FIG. 12 is a side view of an IOL according to another aspect of the present disclosure.

Regarding the at least one haptic engaging the outer surface of the lens capsule, when an IOL is placed anterior to an existing, previously implanted IOL, or when placed anterior to the lens capsule, the at least one haptic can engage the outer surface of the lens capsule. Referring to FIG. 12, the peripheral portion of haptic 52 of an IOL 53 can comprise a hookshaped/substantially J-shaped configuration to engage or curve around an outer surface of a lens capsule. The peripheral end of the peripheral portion can be an atraumatic end so that it does not damage zonules or the lens capsule. The at least one haptic (for example the right haptic and/or the left haptic) can each comprise a plurality of hooks. Hook or substantially J-shaped haptics can allow an IOL to use the force translated from the ciliary muscle to the lens capsule, via the lens zonules, without requiring placement of haptics against elements of the ciliary muscle. Such an embodiment can avoid known potential complications of haptics placed against the ciliary muscle, such as uveitis, glaucoma, and bleeding (e.g. hyphema). Such an embodiment can be implemented in patients that have an already implanted IOL or patients that do not have an already implanted IOL.

Figure 13:
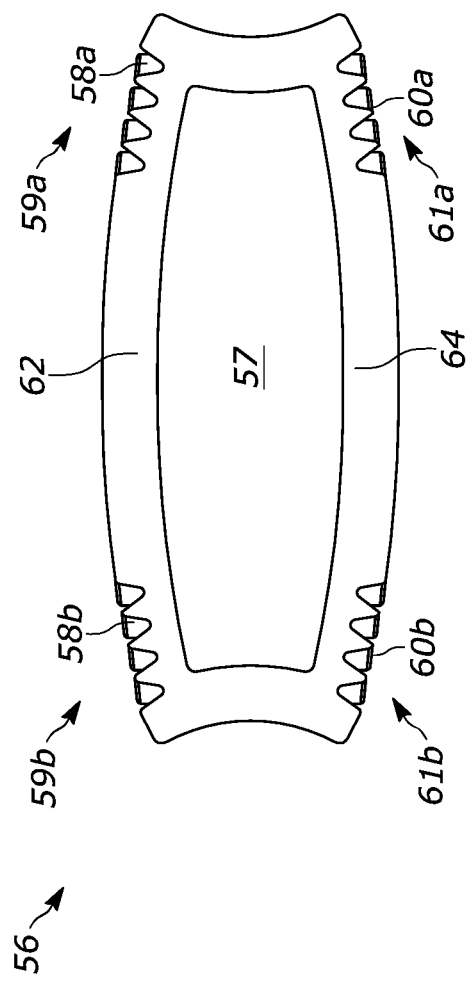
FIG. 13 is a side view of a shape-changing optic of an IOL according to an aspect of the present disclosure.

Referring to FIG. 13, the shape-changing optic itself can define ridges to engage the inner surface of a lens capsule. For example, the shape-changing optic 56 can include an expandable chamber 57, that has an integrated haptic with ridges 58 and 60 on periphery 59 of the anterior face 62 and/or the periphery 61 of the posterior face 64. When tension is placed on the lens capsule by the zonules (e.g. when the ciliary muscle relaxes), the force can be translated (by the ridges engaging the capsule) specifically to the anterior and posterior faces and not just translation of a general force to the entire lens. The anterior face, the posterior face, and/or the side walls can be more resistant to deformational change than the contents of the chamber. This configuration can allow forces from the lens capsule to provide radial tension to the haptics and thus to the anterior face, the anterior face being anterior to the equator of the lens; and/or to provide radial tension to the posterior face, the posterior face being posterior to the equator of the lens. The side walls can be configured to allow for the material in the chamber displaced by the flattening of the anterior face and/or the posterior face to expand into the area of the side wall, thereby allowing the volume of material within the chamber to remain the same.

Figure 14:
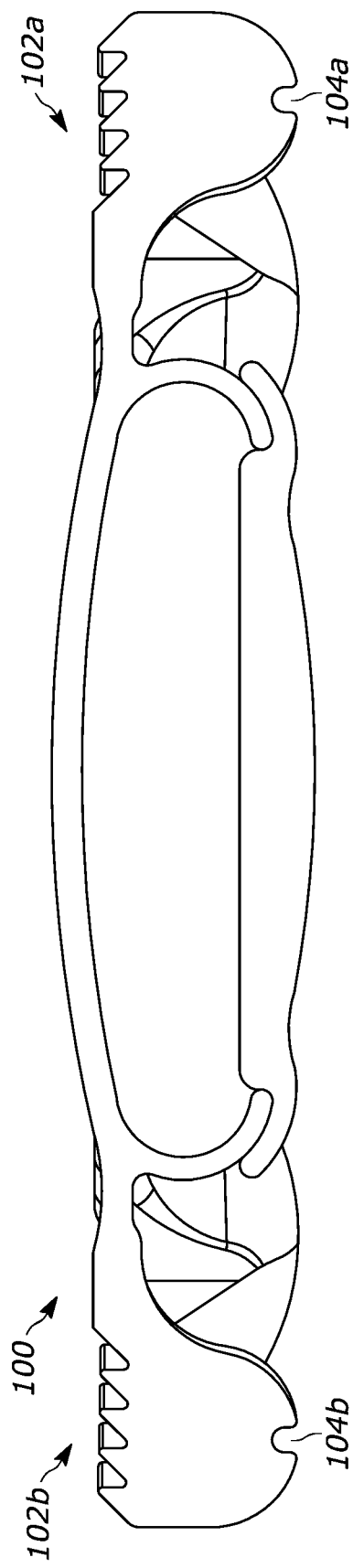
FIG. 14 is a side view of an IOL according to another aspect of the present disclosure.
Figure 15:
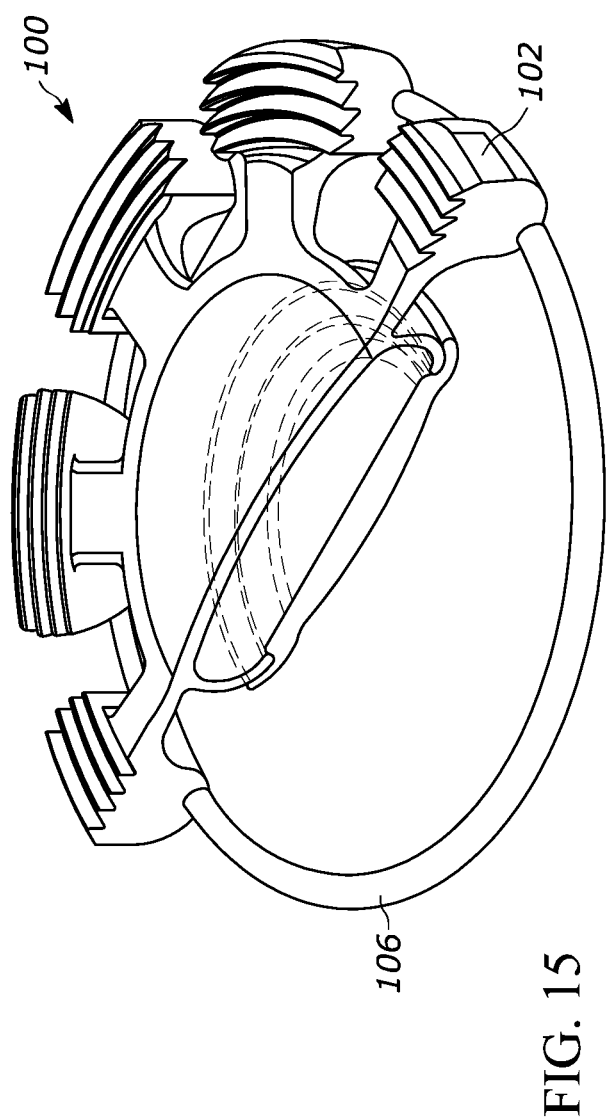
FIG. 15 is a perspective cross-sectional view of the IOL of FIG. 14 according to an aspect of the present disclosure.

Referring to FIGS. 14 and 15, in certain aspects, an IOL 100 is provided where the bottom of haptic 102 defines a recess 104. Such a recess can accommodate a stabilizing ring 106, for example, to keep the haptics from holding inwards with lens capsule fibrosis. Stabilizing ring can be fabricated from any of the materials described above with respect to the anterior and/or posterior faces of the shape changing optic.

The IOL includes an optical axis extending in an anterior-posterior direction and an equator extending in a plane substantially perpendicular to the optical axis. The IOL can further comprise an elastic anterior face located anterior to the equator and a posterior face located posterior to the equator. The anterior face, the posterior face, or both can comprise a poly(dimethylsiloxane) elastomer having a durometer between about 20 Shore A to about 70 Shore A, which is a measure of the hardness of the material. Hardness is related to resistance to deformation change, and therefore the greater the Shore number, the more resistant the material is to deformation. In some embodiments, the elastomer has a durometer between about 20 Shore A to about 50 Shore A. In further embodiments, the durometer can be between about 30 Shore A to about 50 Shore A. In a yet further embodiment, the durometer can be about 50 Shore A. Providing an anterior and posterior face having a suitable hardness allow the material to be stiff enough to displace the fluid in the chamber, strong enough not to tear, and having sufficient elasticity to reshape smoothly over the surface. In some embodiments, the anterior and posterior face are made of material having a tensile strength from about 1.8 mPa to about 8.6 mPa., and more preferably from about 4 mPa to about 6 mPa.

The IOL can further include a chamber located between the anterior face and the posterior face and can comprises a silicone oil comprising polysiloxanes comprising diphenyl siloxane and dimethyl siloxane units. The polysiloxanes can comprise end blocking groups of trimethylsiloxane. The silicone oil can have a maximum viscosity of about 800 $mm^2/s$ at 25° C., including a viscosity between about 400 $mm^2/s$ at 25° C. to about 800 $mm^2/s$ at 25° C. In certain embodiments, the silicone oil can have a mean molecular weight of less than about 3,000 Daltons. It should be noted that this described embodiment can include all the features and aspects described in all other embodiments and aspects of the present disclosure.

An IOL having such features has several advantages. By way of background, in a natural, healthy eye, a lens capsule deforms the lens cortex and lens nucleus (the lens contents) by virtue of the lens cells deforming. This is because the cytosol within each individual lens cell is free flowing and, in aggregate, the lens contents acts like a flowable fluid. Accordingly, the lower the viscosity of the fluid within the chamber of the IOL, the easier it is for the fluid to move in response to force applied by the anterior face and/or the posterior face of the IOL. As such and by way of example with respect to the anterior face, the anterior face comprising a poly(dimethylsiloxane) having a durometer between about 20 Shore A to about 50 Shore A in combination with a chamber containing a silicone oil having a maximum viscosity of about 800 $mm^2/s$ at 25° C. and having a mean molecular weight of less than about 3000 Daltons allows the anterior face to be more resistant to deformational change than the contents of the chamber underlying the anterior face, allows the anterior face to demonstrate elastic properties such as deforming when a force is applied to the anterior face and returning to its original shape when the force is removed resulting in an effective amount of anterior face shape change and therefore accommodating dioptric power change. Such an IOL more closely mimic the elastic gradient of a natural youthful human lens during accommodation particularly when radial tension is directed specifically to at least the anterior face and the tension is directed at points anterior to the equator of the IOL. Further, an anterior and/or posterior face comprising a poly(dimethylsiloxane) having a durometer between about 20 Shore A to about 50 Shore A has sufficient tear strength necessary to mold the lens during manufacturing. In certain embodiments, the IOL can include an elastic side wall extending across the equator and extending from the anterior face to the posterior face. The elastic side wall can also have a durometer between about 20 Shore A to about 50 Shore A, in addition to the anterior face and/or the posterior face having such a durometer value range.

In certain aspects, the present disclosure provides an IOL that has an optical axis extending in an anterior-posterior direction and an equator extending in a plane substantially perpendicular to the optical axis. The IOL can comprise an elastic anterior face located anterior to the equator and a posterior face located posterior to the equator. The anterior face, the posterior face, or both can comprise a polysiloxane that is at least 99% poly(dimethylsiloxane) elastomer. In other words, the polysiloxane can have no phenyl units, trace amounts of phenyl units, or immeasurable amounts of phenyl units such that the IOL achieves its desired functionality as described herein. The IOL can further comprises a chamber located between the anterior face and the posterior face. The chamber can comprise a silicone oil comprising polysiloxanes comprising diphenyl siloxane and dimethyl siloxane units. In certain embodiments, the polysiloxanes comprise at least about 30 mole % diphenyl siloxane, because polymer chains without phenyl groups can absorb into the poly(dimethylsiloxane). In certain embodiments, the IOL can further comprise an elastic side wall extending across the equator and extending from the anterior face to the posterior face wherein the elastic side wall also comprises a polysiloxane that is at least 99% poly(dimethylsiloxane), in addition to the posterior face and/or anterior face having this % poly(dimethylsiloxane). It should be noted that this described embodiment can include all the features and aspects described in all other embodiments and aspects of the present disclosure. An anterior face, posterior face and/or side wall comprising polysiloxane that is at least 99% poly(dimethylsiloxane) minimizes absorption of the silicone oil described herein into the anterior face, the posterior face, and/or the side wall. This is important because absorption of the silicone oil into the anterior face, the posterior face and/or the side wall can increase the thickness and weight of the anterior face, the posterior face and/or the side wall. This can change the mechanical and optical properties of the anterior face, the posterior face and/or the side wall such as the elastic properties, the optical clarity and the refractive index of the IOL.

In some embodiments, at least a portion of the anterior face and the posterior face are coated with a layer of parylene. In some embodiments, the entire anterior face and the posterior face are coated with a layer of parylene, while in further embodiments only the surfaces in contact with silicone oil are coated with parylene. Parylenes are polymers whose backbone consists of para-benzenediyl rings connected by 1,2-ethanediyl bridges. Examples of parylenes include Parylene N, chlorinated parylenes, fluorinated parylenes, and alkyl-substituted parylenes. Preferably only a thin layer of parylene is applied to the optical surfaces in contact with the silicone oil. Parylene provides a barrier to fluid and/or oil absorption into the silicone.

Each of the disclosed aspects and embodiments of the present disclosure may be considered individually or in combination with other aspects and embodiments as well as with respect to other intra-ocular lenses, such as IOLs disclosed in U.S. Pat. No. 10,898,316, which is incorporated by reference in its entirety. In addition, orientations of a shape-changing optic can be modified. For example, when implanted, the lens can be flipped such that the anterior face is facing in a posterior direction and the posterior face is facing in an anterior direction. Further, the IOL can be configured such that it is foldable for insertion. Further, while certain features of embodiments may be shown in only certain figures, such features can be incorporated into or deleted from other embodiments shown in other figures or otherwise disclosed in the specification. Additionally, when describing a range, all points within that range are included in this disclosure.

One aspect of the disclosure is a method of manufacturing an intraocular lens by assembling a bulk polymer material and the silicone oil to form an intraocular lens. The assembling step can comprise advancing the silicone oil into a fluid chamber within the bulk material of the intraocular lens. The silicone oil can have been purified to have a mean molecular weight between about 1,000 Daltons and about 3,000 Daltons. In some embodiments the silicone oil has a refractive index at least 0.2 greater than the bulk polymeric material.

Silicone Oil for the IOL Chamber

The disclosure herein generally relates to fluid, such as silicone oil, that is used in an intraocular lens. While silicone oils used in accommodating IOLs are primary described herein, it is possible to use any of the silicone oils in a non-accommodating IOL. For example, a non-accommodating IOL can have a relatively rigid outer polymeric shell surrounding a silicone oil core. In some embodiments the silicone oil is used in an accommodating intraocular lens that uses movement of the bulk polymeric material enclosing the silicone oil to effect optical power change in the IOL. The silicone oil can, however, be used in non-accommodating intraocular lenses as well.

Swelling of the bulk polymeric material should be taken into consideration when selecting a silicone oil for use in the IOL. When silicone oil is used in accommodating IOL with a bulk material such as a polymeric material, some of the oil components can pass into the bulk material, causing the bulk material to swell. The silicone oil generally needs to be selected or designed in such a way as to avoid adverse interactions with the surrounding bulk IOL material, such as swelling, fogging, dissolving or reacting with the material (e.g., poly acrylate) in some IOLs. The degree of solubility of the silicone oil in the bulk material is dependent on the chemical structure and molecular weight distribution of the silicone oil. Other parameters that influence this interaction are the composition and properties of the bulk material such as homogeneity, chemical structure, hydrophobicity, modulus, and crosslink density. Thus, the silicone oil should have a different composition from the bulk polymer that decreases mixture of the silicone oil with the bulk polymer. For example, if the bulk polymeric material is dimethyl siloxane without phenyl groups, and the silicone oil is a dimethyl/diphenyl siloxane such that an increased percentage of the molecules in the silicone oil contain phenyl groups, then swelling of the bulk dimethyl silicone material is minimized.

The silicone oil included in the IOL should be selected or manufactured to provide one or more advantages such as avoid interaction (e.g. swelling) with the bulk dimethyl polymeric material of the intraocular lens. A variety of traits of the silicone oil can be selected to avoid interaction with the bulk dimethyl polymeric material. These include an increased percentage of diphenyl siloxanes, a silicone oil having a very low level of impurities, an increased amount of long chain silicone molecules, a different molecular weight, and a viscosity and/or refractive index within a preferred range.

Some IOLs rely on or can benefit from a silicone oil comprising diphenyl units. Chain polysiloxanes are composed of difunctional units. The framing groups (R) are either H or organic moieties and the end groups are usually —OR or a monofunctional siloxyl unit. Chain polysiloxanes such as poly-(dimethylsiloxane)s are synthesized by the hydrolysis of dichlorodimethysilane. Diphenyl groups, in with the R group is a phenyl group, can be included in the polysiloxane using essentially the same chemistry. A chemical structure of a polysiloxane including both dimethylsiloxane and diphenyl siloxane is shown in Scheme 1.

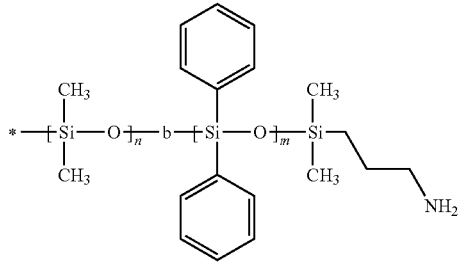

Scheme 1

Dimethyl/diphenyl silicone oils can be produced by increasing the either the percentage of molecules with phenyl groups attached and/or by increasing the number of phenyl groups in each molecule. In some embodiments, each dimethyl/diphenyl copolymer includes at least one phenyl group. Silicone oils with an increased percentage of polysiloxanes including phenyl groups can be used with a pure dimethyl bulk polymeric material. When an increased percentage of the silicone oil includes diphenyl units, the tendency for the silicone oil to be absorbed (swell) into the surrounding dimethyl polysiloxane bulk material is reduced.

Silicone oils including diphenyl units can have a variety of different mole percent of diphenyl units in comparison with the dimethyl units present in the polysiloxane. In some embodiments, the polysiloxane comprises at least 1 mol % diphenyl siloxane, at least 2 mol % diphenyl siloxane, at least 5 mol % diphenyl siloxane, at least 10 mol % diphenyl siloxane, at least 15 mol % diphenyl siloxane, at least 20 mol % diphenyl siloxane, at least 25 mol % diphenyl siloxane, at least 30 mol % diphenyl siloxane, at least 35 mole % diphenyl siloxane, at least 40 mol % diphenyl siloxane, at least 45 mol % diphenyl siloxane, or at least 50 mol % diphenyl siloxane.

The relative amount of diphenyl units included in the polysiloxane can also be expressed as a range, with the reminder of the polysiloxane consisting of dimethyl units. In some embodiments, the silicone oil comprises from about 1 mol % to about 50 mol % diphenyl units, about 1 mol % to about 30 mol % diphenyl units, about 2 mol % to about 50 mol %, about 2 mol % to about 40 mol %, about 5 mol % to about 40 mol %, about 10 mol % to about 40 mol %, about 20 mol % to about 40 mol %, or about 25 mol % to about 35 mol %. In some embodiments, the silicone oil comprises about 30 mol % diphenyl siloxane and about 70 mol % dimethyl siloxane.

The silicone oil preferably also includes a low or very low level of impurities. In some embodiments, the silicone oils described herein have a very low concentration of small cyclic volatile methyl siloxane (cVMS) molecules (e.g., D4-D6 molecules), that include a small number (e.g., 4-6) siloxane groups. The chemical name for the specific D4-D6 molecules are octamethylcyclotetrasiloxane (D4), decamethylcyclopentasiloxane (D5), and dodecamethylcyclosiloxane (D6). It is desirable to have a silicone oil with less than 0.1% of small cyclic species (D4-D6 molecules). In some embodiments, the silicone oil comprises less than 0.05% of small cyclic species (D4-D6 molecules). In addition, the silicone oil should be clear, colorless, have less than about 10 ppm heavy metals and other insoluble inorganics contaminants, and have substantially no silanols.

Removal of silicone oil components that dissolve into the bulk IOL material over time (e.g., during storage) may be accomplished by exposing the silicone oil to bulk quantities of the IOL material, or other materials that have been selected for that purpose. On storage with an appropriate material, the components of the silicone oil that dissolve into the bulk IOL polymeric material may be removed by adjusting the ratio of silicone oil to polymer adsorbent so that sufficiently low levels of those materials remain in the oil.

In may also be desirable to include some long chain polysiloxane molecules in the silicone oil. Long or very long chain polysiloxane molecules can help stabilize the silicone oil and reduce the potential for emulsification. Accordingly, in some embodiments the silicone oil comprises long or very long chain polysiloxane molecules. In some embodiments, the silicone oil comprises from about 5% to about 10% long chain polysiloxane molecules by weight. Long chain polysiloxane molecules (i.e., long chain aralkyl silicone oil) is available from a variety of commercial sources, such as Iota Silicone Oil. Ltd.

In some embodiment's silicone oil is provided that includes smaller polymers having a mean molecular weight of less than about 3,000 Daltons, or between about 1,000 and about 3,000 Daltons. In general, the smaller molecular size of silicone oil polymers correlates with a lower viscosity of the silicone oil. Viscosity relates to the ease with which molecules in a fluid can move past each other, and smaller molecules having a lower molecular weight interact less, causing a decrease in viscosity. It is desirable to have a low viscosity of silicone oil in the fluid chamber of an accommodating IOL to allow a faster response time during accommodation/dis-accommodation. In some embodiments, the silicone oil has a mean molecular weight of less than about 2,500 Daltons. In further embodiments, the silicone oil has a mean molecular weight of less than about 2,000 Daltons. In further embodiments, the silicone oil is provided that has a mean molecular weight between about 1,500 and about 3,000 Daltons. In a yet further embodiment, the silicone oil has a mean molecular weight between about 2,000 and about 3,000 Daltons. In an additional embodiment, the silicone oil has a mean molecular weight between about 1,500 and about 2,500 Daltons. In a further embodiment, the silicone oil has a mean molecular weight from about 1,750 to about 2,750 Daltons. In a yet further embodiment, the silicone oil has a mean molecular weight from about 2,000 to about 2,500 Daltons. Higher molecular weight silicone oils can have a correspondingly high viscosity, which can reduce the response time of the accommodating IOL. Use of silicone oils having a lower molecular weight is particularly efficient when paired with a bulk polymeric material that is relatively firm, such as poly(dimethylsiloxane) elastomer having a durometer between about 20 Shore A to about 50 Shore A.

Another property of the silicone oil is its polydispersity index (PDI), which is a measure of the spread of the molecular weights of the silicone oil (i.e., the heterogeneity of sizes of the polymer molecules). The larger the PDI, the broader the range of molecular weights of the polymers. The PDI of the silicone oil used in the IOLs described herein can have a value of 1.5 or more, or 2.0 or more. In some embodiments, the PDI of the silicone oil has a value from about 1.5 to about 2.0, from about 2.0 to about 3.0, or from about 1.5 to about 2.5. In further embodiments, the PDI of the silicone oil has a value from about 2.3 to about 2.7.

In embodiments in which the bulk polymeric material changes shape in response to ciliary muscle forces applied to the lens capsule via the zonules and the accommodating IOL operates dynamically, the IOL must have an appropriate response time. This requires that the viscosity of the silicone oil have certain defined characteristics. Accordingly, in some embodiments the viscosity of the silicone oil is less than about 800 centistokes (cSt) at 25° C. In further embodiments, the silicone oil has a viscosity between about 600 cSt at 25° C. to about 800 cSt at 25° C. In further embodiments, the silicone oil has a viscosity between about 400 cSt at 25° C. to about 800 cSt at 25° C. The viscosity of silicone oil can be determined using, for example, a digital viscometer.

It is desirable in some instances to have a silicone oil with a refractive index greater than the refractive index of the bulk polymeric material. In some embodiments it is desirable to have a silicone oil where the refractive index is at least 0.2 greater than the refractive index of the bulk polymeric material. Note that the refractive index of poly (dimethylsiloxane), which can be used as the bulk polymeric material, has a refractive index of 1.41. A higher refractive index of the silicone oil increases the dioptric power of the IOL, allowing a lower profile (smaller A-P dimension). Dioptic power is a measure of the convergence or divergence of light created by a lens or optical system. In addition, the higher refractive index of the silicone oil allows for small changes in the shape of the bulk polymeric material to result in larger dioptric power changes of the IOL during accommodation/disaccommodation. A higher refractive index of the silicone oil also allows the IOL to have a smaller anterior posterior profile, which facilitates placement of the IOL in the eye through a smaller incision in the eye. Examples suitable for use with a poly(dimethylsiloxane) shell would include a silicone oil with a refractive index of between about 1.45 and about 1.55, or about 1.49 and about 1.53. The refractive index can be determined using a refractometer.

The use of a silicone oil including a higher relative diphenyl content provides a silicone oil having a higher refractive index and can also result in the silicone oil having a lower viscosity which facilitates rapid response times to accommodation/dis-accommodation.

In some embodiments the silicone oil has a chromatic dispersion less than or equal to about 0.035 refractive index units in the visible range of 400 nm to 750 nm at 35° C. In some embodiments the silicone oil components are fully miscible with each other without evidence of phase separation (i.e., cloudiness or suspensions). In some embodiments the silicone oil has greater than 85% transmittance in the range of 400 nm to 1100 nm for about a 1 cm thick fluid sample.

The silicone oil can have a plurality of the characteristics described herein. For example, the accommodating intraocular lens comprising a bulk dimethyl polymeric material can include a silicone oil comprising diphenyl siloxane and dimethyl siloxane with an index of refraction between about 1.49 and about 1.53, a mean molecular weight number average of between about 1,000 Daltons to about 3,000 Daltons, and a viscosity less than about 800 cSt at about 25° C.

The complete disclosure of all patents, patent applications, and publications, and electronically available materials cited herein are incorporated by reference. Any disagreement between material incorporated by reference and the specification is resolved in favor of the specification. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An intraocular lens (IOL) having an optical axis extending in an anterior-posterior direction and an equator extending in a plane substantially perpendicular to the optical axis, the IOL comprising:
   an elastic anterior face located anterior to the equator; a posterior face located posterior to the equator, wherein the anterior face, the posterior face, or both comprises a poly(dimethylsiloxane) elastomer having a durometer between about 20 Shore A to about 50 Shore A; and
   a chamber located between the anterior face and the posterior face comprising a silicone oil comprising polysiloxanes comprising diphenyl siloxane and dimethyl siloxane units, the silicone oil having a maximum viscosity of about 800 cSt at 25° C. and comprising less than 0.1% octamethylcyclotetrasiloxane, decamethylcyclopentasiloxane, and dodecamethylcyclohexasiloxane.

2. The IOL of claim 1, wherein the poly(dimethylsiloxane) elastomer has a durometer of about 50 Shore A.

3. The IOL of claim 1, further comprising an elastic side wall extending across the equator and extending from the anterior face to the posterior face.

4. The IOL of claim 1, wherein the anterior and posterior face of the IOL comprise polysiloxane that is at least 99% poly(dimethylsiloxane) elastomer.

5. The IOL of claim 1, wherein the anterior face and the posterior face have one or more surfaces that are highly smooth.

6. The IOL of claim 1, wherein at least a portion of the anterior face and the posterior face are coated with a layer of parylene.

7. The IOL of claim 1, wherein the polysiloxane comprises at least 10 mol % diphenyl siloxane.

8. The IOL of claim 1, wherein the silicone oil comprises about 30 mol % diphenyl siloxane and about 70 mol % dimethyl siloxane.

9. The IOL of claim 1, wherein the silicone oil comprises from about 5% to about 10% long chain polysiloxane molecules by weight.

10. The IOL of claim 1, wherein the silicone oil has a viscosity between about 400 cSt at 25° C. to about 800 cSt at 25° C.

11. The IOL of claim 1, wherein the silicone oil has a refractive index between 1.49-1.53.

12. The IOL of claim 1, wherein the silicone oil has a mean molecular weight from about 1,000 to about 3,000 Daltons.

* * * * *